United States Patent
Mallard et al.

(10) Patent No.: US 10,925,855 B2
(45) Date of Patent: Feb. 23, 2021

(54) COMPOSITIONS COMPRISING WATER DISPERSIBLE NANOPARTICLES OF A RETINOID COMPOUND

(71) Applicant: GALDERMA RESEARCH & DEVELOPMENT, Biot (FR)

(72) Inventors: Claire Mallard, Mougins (FR); Amel Safia Djedour, Grasse (FR)

(73) Assignee: GALDERMA RESEARCH & DEVELOPMENT, Biot (FR)

( * ) Notice: Subject to any disclaimer, the term of this patent is extended or adjusted under 35 U.S.C. 154(b) by 0 days.

(21) Appl. No.: 15/739,041

(22) PCT Filed: Jun. 23, 2016

(86) PCT No.: PCT/EP2016/064541
§ 371 (c)(1),
(2) Date: Dec. 21, 2017

(87) PCT Pub. No.: WO2016/207280
PCT Pub. Date: Dec. 29, 2016

(65) Prior Publication Data
US 2018/0185329 A1    Jul. 5, 2018

(30) Foreign Application Priority Data

Jun. 23, 2015 (EP) .................................. 15305970.4

(51) Int. Cl.
*A61K 31/40* (2006.01)
*A61K 9/14* (2006.01)
(Continued)

(52) U.S. Cl.
CPC ............ *A61K 31/40* (2013.01); *A61K 9/0014* (2013.01); *A61K 9/06* (2013.01); *A61K 9/143* (2013.01);
(Continued)

(58) Field of Classification Search
None
See application file for complete search history.

(56) References Cited

U.S. PATENT DOCUMENTS 5,643,584 A * 7/1997 Farng ..................... A61K 8/671
424/401
2003/0108616 A1 * 6/2003 Bosch ..................... A61K 9/145
424/497

(Continued)

FOREIGN PATENT DOCUMENTS

EP          2583665 A2     4/2013
WO    WO-2006066978 A1 *  6/2006  ........... C07C 229/52

(Continued)

OTHER PUBLICATIONS

International Search Report and Written Opinion dated Jul. 26, 2016 corresponding to International Patent Application No. PCT/EP2016/064541, 11 pages.

*Primary Examiner* — Dominic Lazaro
(74) *Attorney, Agent, or Firm* — Foley & Lardner LLP; Sunil Talapatra

(57) ABSTRACT

A composition or nanosuspension is described that includes water dispersible nanoparticles of a retinoid compound having an average particle size of less than about 500 nm. Also described, are pharmaceutical compositions intended for topical administration, including such a composition or nanosuspension. Uses of such pharmaceutical compositions in the treatment of skin diseases, particularly acne, ichthyosis and psoriasis are also described.

19 Claims, 2 Drawing Sheets

Reference micronized Compound A

Gel composition 1-1

Figure 1:
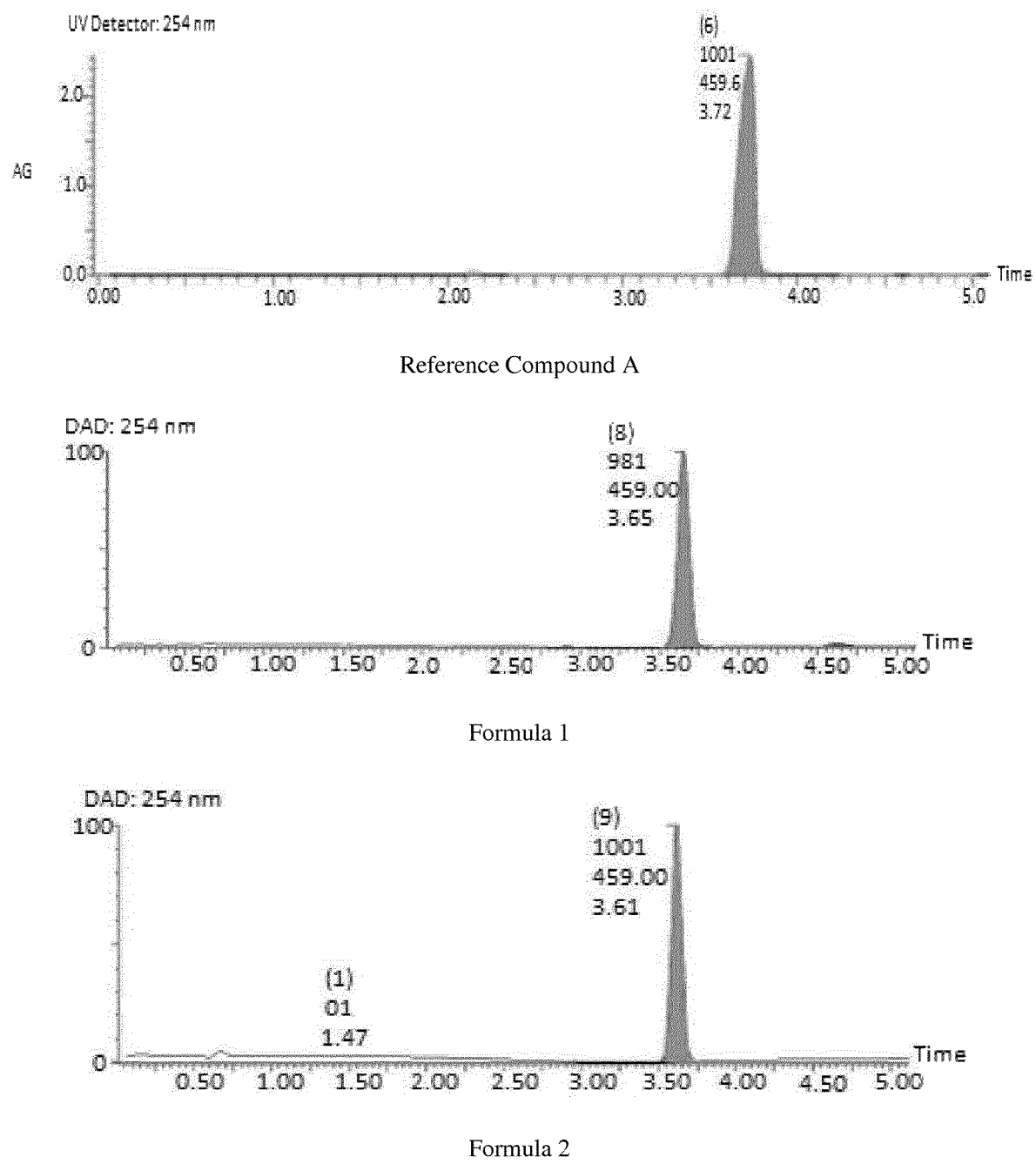

(51) Int. Cl.
*A61K 9/00* (2006.01)
*A61K 9/06* (2006.01)
*A61P 17/00* (2006.01)
*A61K 31/203* (2006.01)
*A61K 9/51* (2006.01)
*A61K 47/32* (2006.01)
*A61K 31/192* (2006.01)
*A61K 31/11* (2006.01)
*A61K 31/07* (2006.01)

(52) U.S. Cl.
CPC .............. *A61K 9/145* (2013.01); *A61K 9/146* (2013.01); *A61K 9/5138* (2013.01); *A61K 31/07* (2013.01); *A61K 31/11* (2013.01); *A61K 31/192* (2013.01); *A61K 31/203* (2013.01); *A61K 47/32* (2013.01); *A61P 17/00* (2018.01)

(56) References Cited

U.S. PATENT DOCUMENTS

| | | | |
|---|---|---|---|
| 2008/0175810 A1* | 7/2008 | Zhang | A61K 8/042 424/78.05 |
| 2012/0195947 A1 | 8/2012 | Perumal et al. | |
| 2015/0125520 A1* | 5/2015 | Mallard | A61K 9/0014 424/451 |

FOREIGN PATENT DOCUMENTS

| | | | | |
|---|---|---|---|---|
| WO | 2013/178749 A1 | 12/2013 | | |
| WO | WO-2013178749 A1 * | 12/2013 | ........... | A61K 9/0014 |

* cited by examiner

Reference micronized Compound A            Gel composition 1-1

COMPOSITIONS COMPRISING WATER DISPERSIBLE NANOPARTICLES OF A RETINOID COMPOUND

CROSS-REFERENCE TO PRIOR APPLICATIONS

This application is a National Stage of PCT/EP2016/064541, filed Jun. 23, 2016, and designating the United States (published on Dec. 29, 2016, as WO 2016/207280 A1), which claims priority under 35 U.S.C. § 119 to European Application No. 15305970.4, filed Jun. 23, 2015, each hereby expressly incorporated by reference in its entirety and each assigned to the assignee hereof.

FIELD OF THE INVENTION

The present invention concerns compositions comprising water dispersible nanoparticles of a retinoid compound and their uses in pharmaceutical compositions for treating dermatological diseases.

BACKGROUND OF THE INVENTION

Retinoid compounds are currently used in the treatment of many dermatological conditions and have been proved as particularly effective in the treatment of skin disease such as acne and psoriasis. However, the topical use of retinoid compounds cause many side effects for the patient. Particularly, treatments with retinoid compounds can cause skin dryness, irritation, erythema, desquamation or skin peeling and tingling or burning for treated patients, and usually require the additional use of wetting agents such as moisturizers, humectants and emollients to alleviate the patient.

The use of a dosage form such as an aqueous gel, water in oil emulsion, solution or spray, wherein the retinoid compound is homogenously dispersed in a liquid medium comprising additional wetting agents appears to be a promising way to try to minimize the irritation and to improve a progressive skin penetration.

However, achieving this type of homogeneous suspension in the usual formulation conditions presented many drawbacks. In particular, they which have not yielded the expecting homogenous suspension of the retinoid compound. Indeed, the use of one or mixture of wetting agent has not resulted in a homogenous suspension, i.e. a good dispersion of the retinoid particles in the liquid medium. This implementation has rather led to partial solubilization of the retinoid compound, or formation of agglomerates, or physical instability of the composition.

In view of the above, WO 2013/178745 proposed compositions comprising a retinoid compound, a gelling agent, and at least one hydrophobic silica to facilitate the dispersion of this hydrophobic compound into the aqueous phase. These compositions comprise microparticles of retinoids homogenously dispersed in presence of hydrophobic silica and exhibit good physical and chemical stability. However such compositions comprising hydrophobic silica are difficult to implement.

However, there is still a need to develop novel and alternative stable and homogenously dispersed formulations of retinoid for an improved skin penetration while providing good physical and chemical stability without aggregates over time.

SUMMARY OF THE INVENTION

In this context, the inventors developed a novel approach by decreasing the particle size of the retinoid without using hydrophobic silica or any surfactants as stabilizers, and thus provided with novel compositions comprising homogenously dispersed particles of a retinoid compound in a nanometer range.

Accordingly, an object of the present invention is a composition comprising water dispersible nanoparticles of a retinoid compound having an average particle size of less than about 500 nm. Preferably, the nanoparticles of a retinoid compound have an average particle size from about 50 nm to 500 nm, more preferably from about 200 nm to 500 nm, even more preferably from about 250 to 450 nm.

In a particular embodiment, the retinoid compound is chosen among tretinoin, isotretinoin, adapalene, tazarotene, retinol, retinaldehyde, and a compound of formula (I):

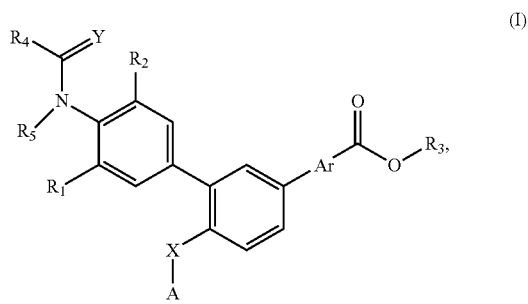

in which:
$R_1$ represents a hydrogen atom, a $C_1$-$C_4$ alkyl group, or a —$CF_3$ group;
$R_2$ represents a hydrogen atom, a $C_1$-$C_1$ alkyl group, a $C_1$-$C_4$ alkoxy group, or a chorine atom;
$R_3$ represents a hydrogen atom, a $C_1$-$C_{10}$ alkyl group or a $C_1$-$C_{10}$ alkoxy group optionally substituted with a methoxy group;
$R_4$ and $R_5$ represent, independently of each other, a hydrogen atom or a $C_1$-$C_3$ alkyl group, or alternatively, $R_4$ and $R_5$ form, together with the bond —N—C(=Y)—, a ring chosen among pyrrolidine, pyrrolidone, piperidine, and piperidone;
Y represents two hydrogen atoms or a heteroatom, preferably an oxygen or a sulphur;
Ar represents a 1,4-phenyl, 2,5-pyridyl, 5,2-pyridyl or 2,5-thiophenyl ring;
X represents an oxygen atom optionally substituted with a $C_1$-$C_4$ alkyl group or a $C_1$-$C_4$ alkylamino group, or a C—C single bond;
A represents a hydrogen atom or the following formula (IA):

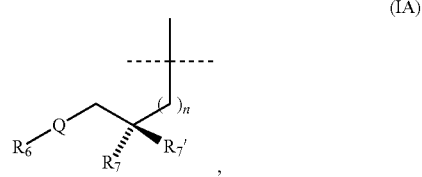

in which:
Q is an oxygen atom or an —NH— bond;
$R_6$ represents a hydrogen atom, a $C_1$-$C_6$ alkyl group, a $C_3$-$C_6$ cycloalkyl group, a —C(O)$CH_3$ group or a —C(O)$CH_2CH_3$ group;

R₇ and R₇' represent, independently of each other, a hydrogen atom, or a hydroxyl group, with the proviso that R₇ and R₇' are not simultaneously a hydroxyl group; and n=0, 1, 2, 3, 4 or 5;

and the optical and geometrical isomers thereof, and the pharmaceutically acceptable salts thereof.

Preferably, the retinoid compound is 3"-tert-butyl-4'-(2-hydroxyethoxy)-4"-pyrrolidin-1-yl[1,1';3',1"]-terphenyl-4-carboxylic acid.

In a further particular embodiment, the composition of the invention comprising nanoparticles of a retinoid compound as above defined further comprises copolymers of vinyl pyrrolidone and vinyl acetate.

In another particular embodiment, the composition of the invention further comprises ethanol, sodium hydroxide, sodium acetate aqueous solution or mixtures thereof.

In a further particular embodiment, the composition of the invention comprises no surfactant. In a preferred embodiment, the composition of the invention comprises:

from about 25% to 35% by weight of a water dispersible nanoparticle of 3"-tert-butyl-4'-(2-hydroxyethoxy)-4"-pyrrolidin-1-yl[1,1';3',1"]-terphenyl-4-carboxylic acid;

from about 55% to 65% by weight of copolymers of vinyl pyrrolidone and vinyl acetate; and from about 0.001% to 10% by weight of sodium hydroxide or sodium acetate;

relative to the total weight of said ingredients.

A further object of the present invention is a process of preparation of a composition of the invention comprising the following step consisting of:

(a) a step of dissolving a retinoid compound and copolymers of vinyl pyrrolidone and vinyl acetate in a solvent;

(b) a step of adding the mixture of step (a) to a solution comprising an antisolvent;

(c) a step of precipitation of the formulation of step (b), thereby forming said retinoid nanoparticles; and (d) an optional step of lyophilization of the solid of step (c).

Preferably, the composition is prepared in a microfluidic based continuous flow reactor.

Another object of the invention is a pharmaceutical composition comprising a composition of the invention, intended to a topical administration.

In a particular embodiment, the pharmaceutical composition is formulated in a gel, an emulsion, a solution, a foam or a lotion form, preferably in a gel form.

In another particular embodiment, the pharmaceutical composition further comprises preservatives.

In a preferred embodiment, the pharmaceutical composition of the invention comprises:

from about 0.001% to 1% by weight of a composition as defined herein; and from about 0.001% to 1% by weight of preservatives;

relative to the total weight of the pharmaceutical composition.

A further object of the invention is the pharmaceutical composition for use in the treatment of skin diseases, preferably acne, ichthyosis and psoriasis.

DETAILED DESCRIPTION OF THE INVENTION

The inventors have surprisingly provided with stable compositions comprising water-dispersible nanoparticles of a retinoid compound highly dispersed without using any wetting agent neither colloidal silica in an aqueous medium. The inventors have also successfully formulated such compositions in physically and chemically stable pharmaceutical compositions, particularly gel formulations, with an efficient skin penetration.

The present invention therefore relates to a composition comprising water dispersible nanoparticles of a retinoid compound having an average particle size of less than about 500 nm.

As used herein the expression "water dispersible nanoparticles of a retinoid compound" means that retinoid particles are homogenously distributed or dispersed in an aqueous medium such as water. Indeed, retinoid compounds in a powder form are difficult to disperse in an aqueous medium due to its hydrophobic properties and the formulation of the retinoid compounds in a nanoparticle form allows to obtain an improved dispersion or distribution in an aqueous medium as disclosed by the present invention, by limiting for instance the formation of aggregates.

The particle size of the retinoid compound is measured by diffraction laser scattering (Nanotrac NPA-250 DLS instrument). By "an average size of less than about 500 nm" is meant that at least 50% of the retinoid nanoparticles have a particle size of less than the average, by number/intensity, i.e., less than about 500 nm, when measured by the above-noted technique.

As used herein, the term "about" will be understood by a person of ordinary skill in the art and will vary to some extent on the context in which it is used. If there are uses of the term which are not clear to persons of ordinary skill in the art given the context in which it is used, "about" will mean up to plus or minus 10% of the particular term, preferably 5%.

Preferably, the water-dispersible nanoparticles of a retinoid compound have an average particle size from about 50 nm to 500 nm, more preferably from about 200 nm to 500 nm, even more preferably from about 250 to 450 nm.

The compositions of the invention comprising said water-dispersible nanoparticles of retinoids correspond to nano-suspensions defined as a biphasic system comprising pure retinoid nanoparticles, which are dispersed in an aqueous vehicle.

The present invention also relates to a water-dispersible nanosuspension of retinoid particles having an average particle size of less than about 500 nm, preferably from about 50 nm to 500 nm, more preferably from about 200 nm to 500 nm, even more preferably from about 250 to 450 nm.

Retinoid Compounds

As used in the present invention, a retinoid compound includes any compound belonging to the class of retinoids. By examples of retinoid compounds, tretinoin, also called retinoic acid, isotretinoin, also called 13-cis retinoic acid, adapalene, tazarotene, retinol, retinaldehyde, or any retinoid compounds as disclosed in the international application WO 2006/006978, the disclosure of which being incorporated herein by reference.

Preferred retinoid compounds according to the invention are disclosed in WO 2006/006978 and are represented by the following formula (I):

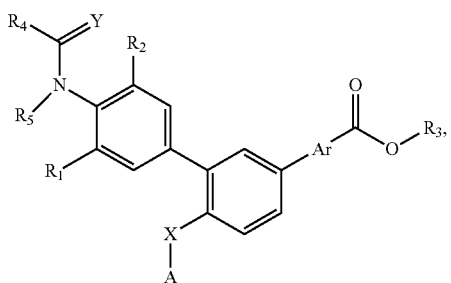

(I)

in which:
R$_1$ represents a hydrogen atom, a C$_1$-C$_4$ alkyl group, or a —CF$_3$ group;
R$_2$ represents a hydrogen atom, a C$_1$-C$_4$ alkyl group, a C$_1$-C$_4$ alkoxy group, or a chorine atom;
R$_3$ represents a hydrogen atom, a C$_1$-C$_{10}$ alkyl group or a C$_1$-C$_{10}$ alkoxy group optionally substituted with a methoxy group;
R$_4$ and R$_5$ represent, independently of each other, a hydrogen atom or a C$_1$-C$_3$ alkyl group, or alternatively, R$_4$ and R$_5$ form, together with the bond —N—C(=Y)—, a ring chosen among pyrrolidine, pyrrolidone, piperidine, and piperidone;
Y represents two hydrogen atoms or a heteroatom, preferably an oxygen or a sulphur;
Ar represents a 1,4-phenyl, 2,5-pyridyl, 5,2-pyridyl or 2,5-thiophenyl ring;
X represents an oxygen atom optionally substituted with a C$_1$-C$_4$ alkyl group or a C$_1$-C$_4$ alkylamino group, or a C—C single bond;
A represents a hydrogen atom or the following formula (IA):

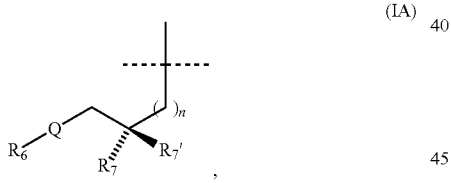

(IA)

in which:
Q is an oxygen atom or an —NH— bond;
R$_6$ represents a hydrogen atom, a C$_1$-C$_6$ alkyl group, a C$_3$-C$_6$ cycloalkyl group, a —C(O)CH$_3$ group or a —C(O)CH$_2$CH$_3$ group;
R$_7$ and R$_{7'}$ represent, independently of each other, a hydrogen atom, or a hydroxyl group, with the proviso that R$_7$ and R$_{7'}$ are not simultaneously a hydroxyl group; and
n=0, 1, 2, 3, 4 ou 5;
and the optical and geometrical isomers thereof, and the pharmaceutically acceptable salts thereof.

According to the present invention, the terms below have the following meanings:

The terms mentioned herein with prefixes such as for example C$_1$-C$_3$ or C$_1$-C$_4$ or C$_1$-C$_6$ or C$_1$-C$_{10}$ can also be used with lower numbers of carbon atoms such as C$_1$-C$_2$ or C$_1$-C$_3$ or C$_1$-C$_5$ or C$_1$-C$_9$. If, for example, the term C$_1$-C$_3$ is used, it means that the corresponding hydrocarbon chain may comprise from 1 to 3 carbon atoms, especially 1, 2 or 3 carbon atoms. If, for example, the term C$_1$-C$_6$ is used, it means that the corresponding hydrocarbon chain may comprise from 1 to 6 carbon atoms, especially 1, 2, 3, 4, 5 or 6 carbon atoms.

The term "alkyl" refers to a saturated, linear or branched aliphatic group. The term "(C$_1$-C$_3$)alkyl" more specifically means methyl (also called "Me"), ethyl (also called "Et"), propyl, or isopropyl, the term "(C$_1$-C$_6$) alkyl" more specifically means methyl, ethyl, propyl, isopropyl, butyl, isobutyl or tert-butyl, pentyl or hexyl.

The term "cycloalkyl" corresponds to the alkyl group defined hereinabove in which the two extremities are bounded. "C$_3$-C$_6$ cycloalkyl" includes for instance cyclopropyl, cyclobutyl, cyclopentyl, cyclohexyl.

The term "halogen" corresponds to a fluorine, chlorine, bromine, or iodine atom.

The term "alkoxy" or "alkyloxy" corresponds to the alkyl group defined hereinabove bonded to the molecule by an —O— (ether) bond. For instance, (C$_1$-C$_6$)alkoxy includes methoxy, ethoxy, propyloxy, isopropyloxy, butyloxy, isobutyloxy, tert-butyloxy, pentyloxy and hexyloxy.

The term "Ar" or "aryl" is a mono- or bi-cyclic aromatic having from 6 to 12 carbon atoms, optionally substituted. Aryl may be a phenyl (also called "Ph"), biphenyl or naphthyl. In a preferred embodiment, the aryl is a phenyl. As used herein, the term "Ar" also includes heteroaryl, which corresponds to a mono- or polycyclic aromatic having from 6 to 14 atoms with at least one heteroatom as defined below. Examples of such mono- and poly-cyclic heteroaryl group may be: pyridyl, dihydroypyridyl, thiazolyl, thiophenyl, furanyl, azocinyl, pyranyl, pyrrolyl, pyrazolyl, imidazolyl, triazolyl, tetrazolyl, benzofuranyl, thianaphthalenyl, indolyl, indolenyl, quinolinyl, isoquinolinyl, benzimidazolyl, pyrrolinyl, tetrahydroquinolinyl, tetrahydroisoquinolinyl, triazinyl, 6H-1,2,5-thiadiazinyl, 2H, 6H-1,5,2-dithiazinyl, thianthrenyl, isobenzofuranyl, chromenyl, xanthenyl, phenoxanthinyl, 2H-pyrrolyl, isothiazolyl, isoxazolyl, pyrazinyl, pyridazinyl, indolizinyl, isoindolyl, 3H-indolyl, 1-Hindazolyl, purinyl, 4H-quinolizinyl, phtalazinyl, naphthyridinyl, quinoxalinyl, quinazolinyl, cinnolinyl, pteridinyl, 4aH-carbazolyl, carbazolyl, β-carbolinyl, phenanthridinyl, acridinyl, pyrimidinyl, phenanthrolinyl, phenazinyl, phenothiazinyl, furazanyl, phenoxazinyl, isochromanyl, chromanyl, imidazolidinyl, imidazolinyl, pyrazolidinyl, pyrazolinyl, indolinyl, isoindolinyl, oxazolidinyl, benzotriazolyl, benzisoxazolyl, oxindolyl, benzoxazolinyl, benzothienyl, benzothiazolyl, isatinyl, dihydropyridyl, pyrimidinyl, pyrazinyl, s-triazinyl, oxazolyl, thiofuranyl. In a preferred embodiment, the heteroaryl is a pyridyl or a thiophenyl.

The term "heteroatom" corresponds to any atom that is not carbon or hydrogen such as nitrogen, oxygen or sulphur atom. Preferred heteroatoms are oxygen or sulphur.

A more preferred retinoid compound of the invention is 3"-tert-butyl-4'-(2-hydroxyethoxy)-4"-pyrrolidin-1-yl[1,1'; 3',1"]-terphenyl-4-carboxylic acid.

Stabilizers—Solvents

The nanosuspensions or compositions of the invention can further comprise copolymers, particularly copolymers of vinyl pyrrolidone and vinyl acetate as stabilizer for preventing the aggregation of the generated particles. The stabilizer is selected according to the nature of the active pharmaceutical ingredient and the solvents/anti-solvents are selected to provide with stable water-dispersible retinoid nanosuspensions. However, in the context of the invention, the stabilizer cannot be a surfactant or hydrophobic silica. Indeed, surfactants may both promote a chemical instability and a crystal growth of nanoparticles in the compositions or nanosuspensions.

A solvent is considered as "solvent" when the retinoid compound and the stabilizer are soluble in it. An anti-solvent is considered as "anti-solvent" when only the retinoid compound is practically insoluble, but the stabilizer must be soluble in it. The solvents and the anti-solvents must be miscible each other.

The inventors defined that a suitable stabilizer for a retinoid compound, particularly 3"-tert-butyl-4'-(2-hydroxyethoxy)-4"-pyrrolidin-1-yl[1,1';3',1"]-terphenyl-4-carboxylic acid, is notably copolymers of vinyl pyrrolidone and vinyl acetate (Luviskol VA64). Suitable solvents/anti-solvents for a retinoid compound, particularly 3"-tert-butyl-4'-(2-hydroxyethoxy)-4"-pyrrolidin-1-yl[1,1';3',1"]-terphenyl-4-carboxylic acid, are typically ethanol and an aqueous solution of sodium hydroxide or of sodium acetate. Preferred anti-solvents according to the invention are a 0.001-0.1M NaOH aqueous solution, typically a 0.001 M, 0.01 M and 0.1 M NaOH aqueous solution, or a 0.5 mg/mL NaOAc aqueous solution.

Accordingly, a particular embodiment of the invention is a composition or nanosuspension as defined above further comprising copolymers of vinyl pyrrolidone and vinyl acetate. A further particular embodiment of the invention is a composition or nanosuspension as defined above further comprising ethanol, water and mixtures thereof.

A preferred embodiment of the invention is a composition or nanosuspension as defined above comprising:
from about 25% to 35% by weight of a water dispersible nanoparticle of 3"-tert-butyl-4'-(2-hydroxyethoxy)-4"-pyrrolidin-1-yl[1,1';3',1"]-terphenyl-4-carboxylic acid;
from about 55% to 65% by weight of copolymers of vinyl pyrrolidone and vinyl acetate; and
from about 0.001% to 10% by weight of sodium hydroxide or sodium acetate; relative to the total weight of said ingredients.

Process of Preparation

A further objet of the invention is a process of preparation of a composition as defined above, comprising the following step consisting of:
(a) a step of dissolving a retinoid compound and copolymers of vinyl pyrrolidone and vinyl acetate in a solvent;
(b) a step of adding the mixture of step (a) to a solution comprising an antisolvent;
(c) a step of precipitation of the formulation of step (b), thereby forming said retinoid nanoparticles; and
(d) an optional step of lyophilization of the solid of step (c).

Particularly, the compositions or the nanosuspensions of the invention are prepared in a microfluidic based continuous flow reactor. More particularly, the steps (a) and (b) are performed by a technology using a microfluidic based continuous flow reactor as disclosed by Nangenex in the international application WO 2009/133418, the disclosure of which being incorporated herein by reference. Such device is built by a first feeding unit followed by at least two heatable reactors with an interjacent cooling unit and a mixing chamber and an interjacent second feeding unit. In the context of the present invention, a mixture of a retinoid compound and copolymers of vinyl pyrrolidone and vinyl acetate in ethanol is pumped by HPLC pumps into the first reactor to be mixed to a solution comprising an antisolvent in a confluent T element called mixing chamber. The second reactor and the interjacent second feeding unit enable modification of the nanoparticles prepared within. This modification step can be repeated by addition of a further mixing chamber, a further feeding unit and a further reactor. The retinoid nanoparticles are continuously produced at atmospheric pressure due to the chemical precipitation by water passed into the mixing unit. The produced colloidal solution is driven through the second reactor unit getting to the dynamic light scattering unit integrated to the device, which can detect the particle size of the obtained nanoparticle continuously. Such device is notably represented in FIG. 1 of the application WO 2009/133418.

The process of the invention may also comprises one optional step of lyophilization (d) in a view to obtain a powder comprising the nanoparticles of a retinoid compound. The nanosuspension obtained at step (b) is precipitated (step (c)) and then lyophilized (step (d)) to give a solid powder comprising retinoid nanoparticles. The retinoid particles obtained by the process as above disclosed have an average particle size of less than about 500 nm, preferably from about 50 nm to 500 nm, more preferably from about 200 nm to 500 nm, and even more preferably from about 250 to 450 nm.

The nanosuspensions or compositions of the invention as above defined, particularly prepared in a microfluidic based continuous flow reactor, are easily dispersible in water compared to retinoid crude powder. They also do not contain any surfactant as stabilizers, neither wetting agent nor colloidal silica. As shown in the examples, they further exhibit a good stability (i.e., at least three days) and can therefore be formulated in pharmaceutical compositions, particularly dermatological compositions.

Pharmaceutical Composition

A further object of the invention is a pharmaceutical composition, particularly a dermatological composition, comprising a composition or a nanosuspension as defined above in a pharmaceutically acceptable medium.

The pharmaceutical composition is particularly intended to a topical administration. Via the topical route, the pharmaceutical composition of the invention is particularly intended for treating skin and mucous membranes.

In the context of the present invention, the expression "pharmaceutically acceptable medium" means a medium compatible with the skin and mucous membranes.

In the pharmaceutical composition of the invention, the nanosuspension or composition comprising water dispersible nanoparticles of a retinoid compound as above defined is present in an amount from 0.001 to 5%, preferably from 0.001 to 1%, more preferably from 0.001 to 0.5%, even more preferably from 0.01 to 0.5%, by weight relative to the total weight of the pharmaceutical composition.

The pharmaceutical composition of the invention can be provided in any pharmaceutically form normally used for topical application such as solution, spray, lotion, emulsion, foam suspension or gel forms. Preferably, the pharmaceutical composition is formulated in a gel, an emulsion, a solution, a foam or a lotion form. More preferably, the pharmaceutical composition is formulated in a gel form.

According to the formulation in a gel form, the pharmaceutical composition as described herein further comprises a gelling agent or mixture of gelling agents.

A "gelling agent" comprises any suitable compounds for a gel formulation such as:

carbomers including carboxyvinyl polymers, Carbopol 981, Carbopol ETD 2020, Carbopol 980, Carbopol Ultrez 10 NF and Pemulen TR1, marketed by Noveon;

polyacrylamides including polyacrylamide/C13-14 isoparaffin/laureth-7 such as sold by Seppic under the name Sepigel 305, and the mixture acrylamide for instance sodium acrylamide/acryloyldimethyltaurate copolymer/isohexadecane/polysorbate 80 under the name Simulgel 600PHA;

cellulose derivatives including hydroxypropylmethylcellulose, hydroxymethylcellulose, xanthan gums, aluminum/magnesium silicates such as Veegum K or Veegum Ultra resold by Vanderbilt, guar gums and the like; and modified starches such as the modified potato starch sold under the named Structure Solanace.

Preferably, the gelling agent used in the pharmaceutical compositions of the invention is the mixture sodium acrylamide/acryloyldimethyltaurate copolymer/isohexadecane/polysorbate 80, also called Simulgel 600PHA.

Particularly, the gelling agent is present in an amount from 0.001 to 10%, preferably from 0.001 to 5%, more preferably from 1 to 5%, even more preferably from 3 to 5%, by weight relative to the total weight of the pharmaceutical composition.

The pharmaceutical composition of the invention can further comprise preservatives in order to effectively protect the composition against bacterial contamination. Examples of preservatives comprise without limitation methyl paraben, also called methyl parahydroxybenzoate, propyl paraben, also called propyl parahydroxybenzoate, benzalkonium chloride, phenoxyethanol, benzylic alcohol, potassium sorbate, benzoic acid, 2-bromo-2-nitropropane-1,3-diol, also called bronopol, chlorhexidine, chlorocresol and its derivatives, benzoate sodium, ethanol and diazolidinyl urea. Such preservatives can be used alone or in combination.

Preferably, the preservatives used in the pharmaceutical compositions of the invention are methyl parahydroxybenzoate and propyl parahydroxybenzoate.

Particularly, the preservative or the mixture of preservative is present in an amount from 0.001 to 5%, preferably from 0.001 to 2%, more preferably from 0.001 to 1%, even more preferably from 0.01 to 0.5%, by weight relative to the total weight of composition.

In other particular embodiments, the pharmaceutical compositions of the invention can also comprise further excipients such as humectant and chelating agents.

Without limitation, humectants include for instance glycerin such as vegetable glycerin, diglycerin, pentylene glycol, propylene glycol, dipropylene glycol, sorbitol and mixtures thereof. The amount of humectants in the pharmaceutical composition of the invention is from 1 to 40%, preferably from 1 to 20%, more preferably from 1 to 10% by weight, relative to the total weight of the pharmaceutical composition.

Without limitation, chelating agents include for instance EDTA (ethylenediaminetetraacetic acid) and its salts or derivatives, dihydroglycerin, citric acid, tartaric acid, gluconolactone and mixtures thereof. The amount of chelating agents in the pharmaceutical composition of the invention is from 0.001 to 5%, preferably from 0.001 to 1%, more preferably from 0.01 to 1% by weight, relative to the total weight of the pharmaceutical composition.

Preferred pharmaceutical compositions of the invention comprise:

from about 0.001% to 1% by weight of a composition or nanosuspension comprising water dispersible nanoparticles of a retinoid compound as defined above;

from about 0.001% to 1% by weight of preservatives;

relative to the total weight of the pharmaceutical composition.

Particular pharmaceutical compositions of the invention comprise:

from about 0.001% to 1% by weight of a composition or nanosuspension comprising water dispersible nanoparticles of a retinoid compound as defined above;

from about 1 to 10% by weight of humectants;

from about 0.01 to 1% by weight of chelating agents; and from about 0.001% to 1% by weight of preservatives;

relative to the total weight of the pharmaceutical composition.

The pharmaceutical compositions as defined above exhibit good homogeneity and a high stability. As demonstrated by example 2 and FIG. 3, no crystal growth and no aggregates appear over time showing thereby good physical stability. Also, the retinoid compound, particularly 3"-tert-butyl-4'-(2-hydroxyethoxy)-4"-pyrrolidin-1-yl[1,1';3',1"]-terphenyl-4-carboxylic acid remains chemically stable over time. In addition, the pharmaceutical compositions of the invention have a good skin penetration and a compartmental distribution in epidermis and dermis similar to both micronized and solubilized retinoid gel references.

Another object of the invention is a pharmaceutical composition as above defined, for use in the treatment of skin diseases or dermatologic conditions.

A further object of the invention is a use of a nanosuspension or composition of the invention for the manufacture of a pharmaceutical composition as above defined for treating skin diseases or dermatologic conditions.

A further object of the invention is a method for treating skin diseases or dermatologic conditions in a subject in need thereof, comprising administering a pharmaceutical composition as above defined in an effective amount.

As used herein, the term "treatment", "treat" or "treating" refers to any act intended to ameliorate the health status of patients such as therapy, prevention, prophylaxis and retardation of the skin disease. In certain embodiments, such term refers to the amelioration or eradication of a disease or symptoms associated with a skin disease. In other embodiments, this term refers to minimizing the spread or worsening of the disease resulting from the administration of one pharmaceutical composition of the invention to a subject with such skin disease.

By "effective amount" it is meant the quantity of the pharmaceutical composition of the invention which, prevents, removes, or reduces the deleterious effects of the treated skin disease in the patient suffering from such skin disease. It is understood that the administered dose may be adapted by those skilled in the art according to the patient, the type of skin disease, the mode of administration, etc.

In the context of the present invention, a skin disease typically comprises without limitation:

dermatological complaints associated with a keratinization disorder relating to differentiation and proliferation, especially for treating acne, particularly, common acne, comedones, polymorphonuclear leukocytes, acne rosacea, nodulocystic acne, acne conglobata, senile acne, secondary acnes such as solar acne, medication-related acne or occupational acne;

keratinization disorder, especially ichthyosis, ichtyosiform conditions, Darier's disease, palmoplantar keratoderma, leukoplakia and leukoplakiform conditions, and cutaneous or mucous (buccal) lichen;

dermatological complaints associated with a keratinization disorder with an inflammatory and/or immunoallergic component, and especially all forms of psoriasis, whether cutaneous, mucous or ungual psoriasis, and even psoriatic rheumatism, or cutaneous atopy, such as eczema, or respiratory atopy, or even gingival hypertrophy;

dermal or epidermal proliferations, whether benign or malignant, and whether of viral origin or otherwise, such as common warts, flat warts, molluscum contagiosum and verruciform epidermodysplasia, oral or florid papillomatoses and proliferations that may be induced by ultraviolet radiation, especially in the case of actinic keratosis;

pathology associated with chronological or actinic ageing;

cicatrization disorders and skin ulcers;

sebaceous function disorders such as the hyperseborrhoea of acne or simple seborrhoea;

complaint of fungal origin on the skin, such as *tinea pedis* and *tinea versicolor;* dermatological complaints with an immunological component;

skin disorders caused by exposure to UV rays; and dermatological complaints associated with inflammation or infection of the tissues surrounding the hair follicles, caused especially by microbial colonization or infection, especially impetigo, seborrhoeic dermatitis, folliculitis or sycosis barbae, or involving any other bacterial or fungal agent.

In a preferred embodiment, skin diseases are acne, ichthyosis and psoriasis.

LEGEND TO THE FIGURES

FIG. 1: HPLC chromatograms of reference 3"-tert-butyl-4'-(2-hydroxyethoxy)-4"-pyrrolidin-1-yl[1,1';3',1"]-terphenyl-4-carboxylic acid (compound A), formula 1 and formula 2.

Figure 2:
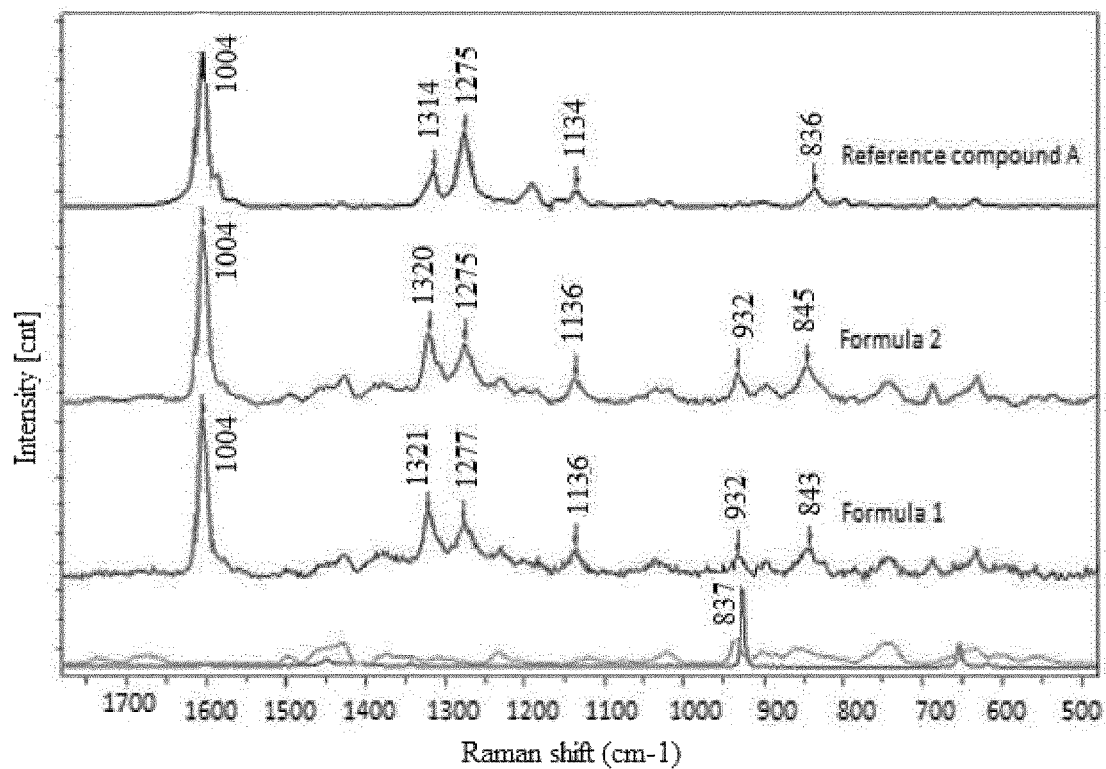

FIG. 2: Raman analysis of reference 3"-tert-butyl-4'-(2-hydroxyethoxy)-4"-pyrrolidin-1-yl[1,1';3',1"]-terphenyl-4-carboxylic acid (compound A), formula 1 and formula 2.

Figure 3:
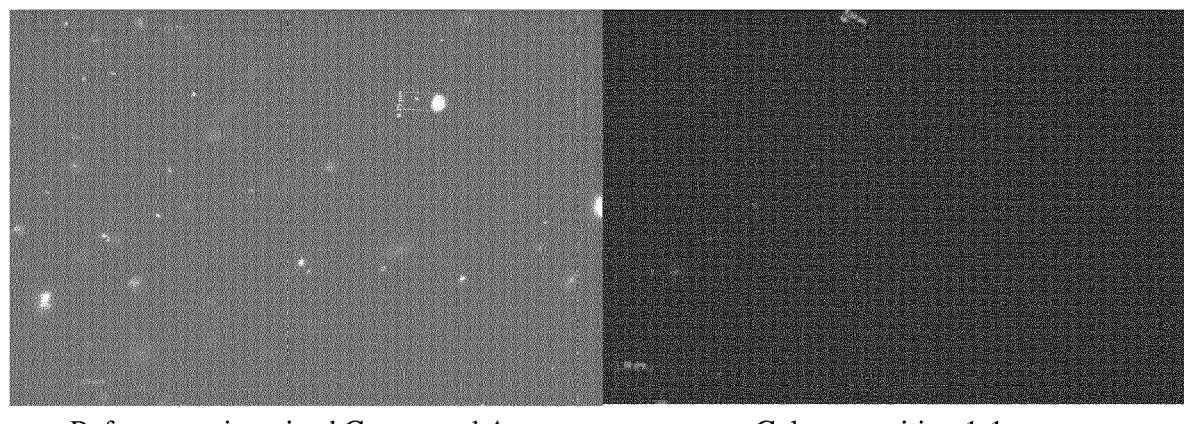

FIG. 3: Microscopic observation of reference micronized 3"-tert-butyl-4'-(2-hydroxyethoxy)-4"-pyrrolidin-1-yl[1,1'; 3',1"]-terphenyl-4-carboxylic acid (compound A) and gel composition 1-1 of the invention Further aspects and advantages of the invention will be disclosed in the following experimental section.

EXAMPLES

Example 1: Compositions/Nanosuspensions of the Invention

1. Solvent Screening

Method 10-20 mg of 3"-tert-butyl-4'-(2-hydroxyethoxy)-4"-pyrrolidin-1-yl[1,1';3',1"]-terphenyl-4-carboxylic acid (hereinafter "compound A") was placed into a 30 ml vial. 200 µl of the selected solvent was added and the vial was stirred by magnetic stirring.

If the compound A was not dissolved, the vial was placed into ultrasonic bath with mild heating.

If the compound A was still not dissolved, further 200 µl of the solvent was added to the vial and the magnetic stirring and ultrasonication were repeated.

The whole procedure (addition of the solvent, stirring, ultrasonication, heating) was repeated stepwise until every compound A particles was dissolved and a clear, translucent liquid was obtained.

Results

The results are summarized in Table 1.

TABLE 1

| Solvent | Solubility (mg/ml) | Method |
|---|---|---|
| Methanol | 1.7 | Sonication, RT* |
| Ethanol | 4.9 | Sonication, RT |
| Isopropanol | 3.0 | Sonication, RT |
| Acetone | 3.0 | Sonication, RT |
| Acetonitrile | 0.4 | Sonication, RT |
| Tetrahydrofuran | 30.5 | Sonication, RT |
| Pyridine | 34.5 | Sonication, RT |
| Water | <<0.05 | Sonication, T = 45° C. |

*Room temperature

The compound A showed favorable solubility profile; the compound was very slightly soluble in acetonitrile, slightly soluble in methanol, ethanol, isopropanol, acetone and it was soluble in tetrahydrofuran and pyridine.

The compound A was practically insoluble in water.

2. Precipitation Test

Method:

1 mg/ml solutions of compound A were prepared in each appropriate solvent. Under vigorous stirring, the anti-solvent was added dropwise to the active solution.

If precipitation occurred for less than tenfold anti-solvent, this solvent/anti-solvent was used for the stabilizer screening.

If precipitation did not occur, the concentration of the compound A solution was increased.

Solutions containing 2, 4, 8, 12, 20 and 50 mg/ml of compound A were tested if the previous concentration proved to be insufficient.

Results:

The precipitation tests were performed after solvent screening. Compound A precipitated from every tested organic solvent at 1 mg/mL concentration, thus all solvents were used for stabilizer screening.

3. Stabilizer Screening

Method 1 mg/ml of compound A solutions were prepared in all appropriate solvent containing 2 mg/ml stabilizer. Under vigorous stirring, the anti-solvent solution of the active ingredient was added to the solution of the active ingredient.

Criteria of the Stabilizer Selection:

If precipitation did not occur, other stabilizers were tested.

If precipitation occurred, the size of the nanoparticles was measured by DLS (Dynamic Light Scattering) and the stability of the colloid solution was monitored. If the colloid solution was stable over 2 hours (no aggregation, sedimentation, crystal forming), and no aggregation occurred, the sample was lyophilized.

If precipitation occurred, however the colloid solution was not stable over the whole solid formulation procedure, other stabilizers were tested.

Results

The results are summarized in tables 2 and 3.

TABLE 2

| Compound A (mg) | Stabilizer | Solvent | Anti-solvent | Observation |
|---|---|---|---|---|
| 1.0 | — | 1 mL MeOH | 4 mL water | Aggregated |
| 1.0 | 2 mg PVP10 | 1 mL MeOH | 4 mL water | Precipitation did not occur |
| 1.0 | 2 mg PVP40 | 1 mL MeOH | 4 mL water | Precipitation did not occur |
| 1.0 | 2 mg PVPK90 | 1 mL MeOH | 4 mL water | Precipitation did not occur |
| 1.0 | 2 mg Pluronic PE6800 | 1 mL MeOH | 4 mL water | Cloudy immediately |
| 1.0 | 2 mg Pluronic PE10500 | 1 mL MeOH | 4 mL water | Cloudy immediately |
| 1.0 | 2 mg Lutrol F 127 | 1 mL MeOH | 4 mL water | Cloudy immediately |
| 1.0 | 2 mg Tetronic | 1 mL MeOH | 4 mL water | Cloudy immediately |
| 1.0 | 2 mg PEG2000 | 1 mL MeOH | 4 mL water | Aggregated |
| 1.0 | 2 mg PEG6000 | 1 mL MeOH | 4 mL water | Aggregated |
| 1.0 | 2 mg PEOX50 | 1 mL MeOH | 4 mL water | Aggregated |
| 1.0 | 2 mg PEOX500 | 1 mL MeOH | 4 mL water | Aggregated |
| 1.0 | 2 mg Luviskol VA64 | 1 mL MeOH | 4 mL water | Aggregated after 25 min |
| 1.0 | 2 mg TPGS | 1 mL MeOH | 4 mL water | Aggregated after 25 min |
| 1.0 | 2 mg Soluplus | 1 mL MeOH | 4 mL water | Precipitation did not occur |
| 1.0 | 2 mg PMAMVE | 1 mL MeOH | 4 mL water | Aggregated |
| 1.0 | 2 mg Solutol | 1 mL MeOH | 4 mL water | Aggregated |
| 1.0 | 2 mg Klucel LF | 1 mL MeOH | 4 mL water | Aggregated |
| 1.0 | 2 mg Klucel EF | 1 mL MeOH | 4 mL water | Aggregated |
| 1.0 | — | 1 mL EtOH | 4 mL water | Aggregated |
| 1.0 | 2 mg PVP10 | 1 mL EtOH | 4 mL water | Colloid, Stable for 30 min |
| 1.0 | 2 mg PVP40 | 1 mL EtOH | 4 mL water | Colloid, Stable for 15 min |
| 1.0 | 2 mg PVPK90 | 1 mL EtOH | 4 mL water | Colloid, Stable for 5 min |
| 1.0 | 2 mg Pluronic PE6800 | 1 mL EtOH | 4 mL water | Aggregated |
| 1.0 | 2 mg Pluronic PE10500 | 1 mL EtOH | 4 mL water | Aggregated |
| 1.0 | 2 mg Lutrol F 127 | 1 mL EtOH | 4 mL water | Aggregated |
| 1.0 | 2 mg Tetronic | 1 mL EtOH | 4 mL water | Aggregated |
| 1.0 | 2 mg PEG2000 | 1 mL EtOH | 4 mL water | Aggregated |
| 1.0 | 2 mg PEG6000 | 1 mL EtOH | 4 mL water | Aggregated |
| 1.0 | 2 mg PEOX50 | 1 mL EtOH | 4 mL water | Colloid, Stable for 10 min |
| 1.0 | 2 mg PEOX500 | 1 mL EtOH | 4 mL water | Aggregated |
| 1.0 | 2 mg Luviskol VA64 | 1 mL EtOH | 4 mL water | Colloid, Stable for 30 min |
| 1.0 | 2 mg TPGS | 1 mL EtOH | 4 mL water | Aggregated |
| 1.0 | 2 mg Soluplus | 1 mL EtOH | 4 mL water | Slightly opalescent colloid, stable for 5 min |
| 1.0 | 2 mg PMAMVE | 1 mL EtOH | 4 mL water | Aggregated |
| 1.0 | 2 mg Solutol | 1 mL EtOH | 4 mL water | Aggregated |
| 1.0 | 2 mg Klucel LF | 1 mL EtOH | 4 mL water | Aggregated |
| 1.0 | 2 mg Klucel EF | 1 mL EtOH | 4 mL water | Aggregated |
| 1.0 | — | 1 mL ACE | 4 mL water | Aggregated |
| 1.0 | 2 mg Pluronic PE6800 | 1 mL ACE | 4 mL water | Aggregated immediately |
| 1.0 | 2 mg Pluronic PE10500 | 1 mL ACE | 4 mL water | Aggregated immediately |
| 1.0 | 2 mg Lutrol F 127 | 1 mL ACE | 4 mL water | Aggregated immediately |
| 1.0 | 2 mg Tetronic | 1 mL ACE | 4 mL water | Aggregated immediately |
| 1.0 | 2 mg PEG2000 | 1 mL ACE | 4 mL water | Aggregated immediately |
| 1.0 | 2 mg PEG6000 | 1 mL ACE | 4 mL water | Aggregated immediately |
| 1.0 | 2 mg PEOX50 | 1 mL ACE | 4 mL water | Aggregated within 5 min |
| 1.0 | 2 mg PEOX500 | 1 mL ACE | 4 mL water | Aggregated within 5 min |
| 1.0 | 2 mg Luviskol VA64 | 1 mL ACE | 4 mL water | Aggregated within 5 min |
| 1.0 | 2 mg TPGS | 1 mL ACE | 4 mL water | Aggregated within 5 min |
| 1.0 | 2 mg Soluplus | 1 mL ACE | 4 mL water | Aggregated within 5 min |
| 1.0 | 2 mg Solutol | 1 mL ACE | 4 mL water | Aggregated immediately |
| 1.0 | — | 1 mL IPA | 4 mL water | Aggregated |
| 1.0 | 2 mg PVP10 | 1 mL IPA | 4 mL water | Aggregated |
| 1.0 | 2 mg PVP40 | 1 mL IPA | 4 mL water | Aggregated |
| 1.0 | 2 mg PVPK90 | 1 mL IPA | 4 mL water | Aggregated |
| 1.0 | 2 mg Pluronic PE6800 | 1 mL IPA | 4 mL water | Aggregated |
| 1.0 | 2 mg Pluronic PE10500 | 1 mL IPA | 4 mL water | Aggregated |
| 1.0 | 2 mg Tetronic | 1 mL IPA | 4 mL water | Aggregated |
| 1.0 | 2 mg PEG2000 | 1 mL IPA | 4 mL water | Aggregated |
| 1.0 | 2 mg PEOX50 | 1 mL IPA | 4 mL water | Aggregated |
| 1.0 | 2 mg PEOX500 | 1 mL IPA | 4 mL water | Aggregated |
| 1.0 | 2 mg Luviskol VA64 | 1 mL IPA | 4 mL water | Aggregated |
| 1.0 | 2 mg TPGS | 1 mL IPA | 4 mL water | Aggregated |
| 1.0 | 2 mg Solutol | 1 mL IPA | 4 mL water | Aggregated |
| 1.0 | 2 mg Klucel LF | 1 mL IPA | 4 mL water | Aggregated |
| 1.0 | 2 mg Klucel EF | 1 mL IPA | 4 mL water | Aggregated |
| 1.0 | 2 mg Pluronic PE6800 | 1 mL THF | 5 mL water | Aggregated |
| 1.0 | 2 mg Pluronic PE10500 | 1 mL THF | 4 mL water | Aggregated |
| 1.0 | 2 mg Lutrol F 127 | 1 mL THF | 5 mL water | Aggregated |
| 1.0 | 2 mg Tetronic | 1 mL THF | 4 mL water | Aggregated |
| 1.0 | 2 mg PEG2000 | 1 mL THF | 4 mL water | Aggregated |
| 1.0 | 2 mg PEOX50 | 1 mL THF | 4 mL water | Aggregated |
| 1.0 | 2 mg PEOX500 | 1 mL THF | 4 mL water | Aggregated |

TABLE 2-continued

| Compound A (mg) | Stabilizer | Solvent | Anti-solvent | Observation |
|---|---|---|---|---|
| 1.0 | 2 mg Luviskol VA64 | 1 mL THF | 4 mL water | Aggregated |
| 1.0 | 2 mg TPGS | 1 mL THF | 4 mL water | Aggregated |
| 1.0 | 2 mg Soluplus | 1 mL THF | 4 mL water | Aggregated |
| 1.0 | 2 mg Solutol | 1 mL THF | 4 mL water | Aggregated |
| 1.0 | 2 mg Klucel LF | 1 mL THF | 4 mL water | Aggregated |
| 1.0 | 2 mg Klucel EF | 1 mL THF | 4 mL water | Aggregated |

Colloids stable for at least 10 minutes were obtained when PVP10 (Poly(vinylpyrrolidone), Mw=10000), PVP40 (Poly(vinylpyrrolidone), Mw=40000), Luviskol VA64 (Vinylpyrrolidone-vinylacetate block copolymer) or PEOX50 (Poly(2-ethyl-2-oxazoline), Mw=5000-7000) was used as stabilizer and ethanol was used as solvent. All stable colloids were solid formulated by lyophilization and solid nanosized compound A powders were obtained. The solid powders wetted well but the resulting colloid solutions were cloudy and sedimentation was observed after a few minutes.

In order to increase the stability of the redispersed colloid solutions the nature of the anti-solvent has been investigated.

TABLE 3

| Compound A (mg) | Stabilizer | Solvent | Anti-solvent | Observation |
|---|---|---|---|---|
| 1.0 | 2 mg PVP10 | 1 mL EtOH | 7 mL 0.5 mg/mL SDS solution | Aggregated within 1 hour |
| 1.0 | 2 mg PVP10 | 1 mL EtOH | 7 mL 0.5 mg/mL DSS solution | Aggregated within 1 hour |
| 1.0 | 2 mg PVP10 | 1 mL EtOH | 7 mL 0.5 mg/mL citric acid solution | Aggregated immediately |
| 1.0 | 2 mg PVP10 | 1 mL EtOH | 7 mL 0.5 mg/mL BAC solution | Aggregated immediately |
| 1.0 | 2 mg PVP10 | 1 mL EtOH | 7 mL 0.5 mg/mL Mannitol solution | Aggregated immediately |
| 1.0 | 2 mg PVP10 | 1 mL EtOH | 7 mL 0.5 mg/mL NaOAc solution | Aggregated immediately |
| 1.0 | 2 mg PVP10 | 1 mL EtOH | 7 mL 0.05 mg/mL SDS solution | Aggregated immediately |
| 1.0 | 2 mg PVP10 | 1 mL EtOH | 7 mL 0.05 mg/mL DSS solution | Aggregated immediately |
| 1.0 | 2 mg PVP10 | 1 mL EtOH | 7 mL 0.05 mg/mL citric acid solution | Aggregated immediately |
| 1.0 | 2 mg PVP10 | 1 mL EtOH | 7 mL 0.05 mg/mL BAC solution | Aggregated immediately |
| 1.0 | 2 mg PVP10 | 1 mL EtOH | 7 mL 0.05 mg/mL Mannitol solution | Aggregated immediately |
| 1.0 | 2 mg PVP10 | 1 mL EtOH | 7 mL 0.05 mg/mL NaOAc solution | Aggregated immediately |
| 1.0 | 2 mg PVP40 | 1 mL EtOH | 7 mL 0.5 mg/mL SDS solution | Aggregated within 1 hour |
| 1.0 | 2 mg PVP40 | 1 mL EtOH | 7 mL 0.5 mg/mL DSS solution | Aggregated within 1 hour |
| 1.0 | 2 mg PVP40 | 1 mL EtOH | 7 mL 0.5 mg/mL citric acid solution | Aggregated immediately |
| 1.0 | 2 mg PVP40 | 1 mL EtOH | 7 mL 0.5 mg/mL BAC solution | Aggregated immediately |
| 1.0 | 2 mg PVP40 | 1 mL EtOH | 7 mL 0.5 mg/mL Mannitol solution | Aggregated immediately |
| 1.0 | 2 mg PVP40 | 1 mL EtOH | 7 mL 0.5 mg/mL NaOAc solution | Aggregated within 1 hour |
| 1.0 | 2 mg PVP40 | 1 mL EtOH | 7 mL 0.05 mg/mL SDS solution | Aggregated immediately |
| 1.0 | 2 mg PVP40 | 1 mL EtOH | 7 mL 0.05 mg/mL DSS solution | Aggregated immediately |
| 1.0 | 2 mg PVP40 | 1 mL EtOH | 7 mL 0.05 mg/mL citric acid solution | Aggregated immediately |
| 1.0 | 2 mg PVP40 | 1 mL EtOH | 7 mL 0.05 mg/mL BAC solution | Aggregated immediately |
| 1.0 | 2 mg PVP40 | 1 mL EtOH | 7 mL 0.05 mg/mL Mannitol solution | Aggregated immediately |
| 1.0 | 2 mg PVP40 | 1 mL EtOH | 7 mL 0.05 mg/mL NaOAc solution | Aggregated immediately |
| 1.0 | 2 mg Luviskol VA64 | 1 mL EtOH | 7 mL 0.5 mg/mL SDS solution | Aggregated within 1 hour |
| 1.0 | 2 mg Luviskol VA64 | 1 mL EtOH | 7 mL 0.5 mg/mL DSS solution | Aggregated within 1 hour |

TABLE 3-continued

| Compound A (mg) | Stabilizer | Solvent | Anti-solvent | Observation |
|---|---|---|---|---|
| 1.0 | 2 mg Luviskol VA64 | 1 mL EtOH | 7 mL 0.5 mg/mL citric acid solution | Aggregated immediately |
| 1.0 | 2 mg Luviskol VA64 | 1 mL EtOH | 7 mL 0.5 mg/mL BAC solution | Aggregated immediately |
| 1.0 | 2 mg Luviskol VA64 | 1 mL EtOH | 7 mL 0.5 mg/mL Mannitol solution | Aggregated immediately |
| 1.0 | 2 mg Luviskol VA64 | 1 mL EtOH | 7 mL 0.5 mg/mL NaOAc solution | Stable for 1 day at RT |
| 1.0 | 2 mg Luviskol VA64 | 1 mL EtOH | 7 mL 0.05 mg/mL SDS solution | Aggregated immediately |
| 1.0 | 2 mg Luviskol VA64 | 1 mL EtOH | 7 mL 0.05 mg/mL DSS solution | Aggregated immediately |
| 1.0 | 2 mg Luviskol VA64 | 1 mL EtOH | 7 mL 0.05 mg/mL citric acid solution | Aggregated immediately |
| 1.0 | 2 mg Luviskol VA64 | 1 mL EtOH | 7 mL 0.05 mg/mL BAC solution | Aggregated immediately |
| 1.0 | 2 mg Luviskol VA64 | 1 mL EtOH | 7 mL 0.05 mg/mL Mannitol solution | Aggregated immediately |
| 1.0 | 2 mg Luviskol VA64 | 1 mL EtOH | 7 mL 0.05 mg/mL NaOAc solution | Aggregated immediately |
| 1.0 | 2 mg PEOX50 | 1 mL EtOH | 7 mL 0.5 mg/mL SDS solution | Aggregated within 1 hour |
| 1.0 | 2 mg PEOX50 | 1 mL EtOH | 7 mL 0.5 mg/mL DSS solution | Aggregated within 1 hour |
| 1.0 | 2 mg PEOX50 | 1 mL EtOH | 7 mL 0.5 mg/mL citric acid solution | Aggregated immediately |
| 1.0 | 2 mg PEOX50 | 1 mL EtOH | 7 mL 0.5 mg/mL BAC solution | Aggregated immediately |
| 1.0 | 2 mg PEOX50 | 1 mL EtOH | 7 mL 0.5 mg/mL Mannitol solution | Aggregated immediately |
| 1.0 | 2 mg PEOX50 | 1 mL EtOH | 7 mL 0.5 mg/mL NaOAc solution | Aggregated within 1 hour |
| 1.0 | 2 mg PEOX50 | 1 mL EtOH | 7 mL 0.05 mg/mL SDS solution | Aggregated immediately |
| 1.0 | 2 mg PEOX50 | 1 mL EtOH | 7 mL 0.05 mg/mL DSS solution | Aggregated immediately |
| 1.0 | 2 mg PEOX50 | 1 mL EtOH | 7 mL 0.05 mg/mL citric acid solution | Aggregated immediately |
| 1.0 | 2 mg PEOX50 | 1 mL EtOH | 7 mL 0.05 mg/mL BAC solution | Aggregated immediately |
| 1.0 | 2 mg PEOX50 | 1 mL EtOH | 7 mL 0.05 mg/mL Mannitol solution | Aggregated immediately |
| 1.0 | 2 mg PEOX50 | 1 mL EtOH | 7 mL 0.05 mg/mL NaOAc solution | Aggregated immediately |
| 1.0 | 3 mg PVP10 | 1 mL EtOH | 7 mL 0.05 mg/mL NaOAc solution | Aggregated immediately |
| 1.0 | 3 mg PVP10 | 1 mL EtOH | 7 mL 0.5 mg/mL NaOAc solution | Aggregated within 1 hour |
| 1.0 | 4 mg PVP10 | 1 mL EtOH | 7 mL 0.05 mg/mL NaOAc solution | Aggregated immediately |
| 1.0 | 4 mg PVP10 | 1 mL EtOH | 7 mL 0.5 mg/mL NaOAc solution | Aggregated within 1 hour |
| 1.0 | 3 mg PVP40 | 1 mL EtOH | 7 mL 0.05 mg/mL NaOAc solution | Aggregated immediately |
| 1.0 | 3 mg PVP40 | 1 mL EtOH | 7 mL 0.5 mg/mL NaOAc solution | Stable for 1 day at RT |
| 1.0 | 4 mg PVP40 | 1 mL EtOH | 7 mL 0.05 mg/mL NaOAc solution | Aggregated immediately |
| 1.0 | 4 mg PVP40 | 1 mL EtOH | 7 mL 0.5 mg/mL NaOAc solution | Aggregated within 1 day |
| 1.0 | 3 mg Luviskol VA64 | 1 mL EtOH | 7 mL 0.05 mg/mL NaOAc solution | Aggregated immediately |
| 1.0 | 3 mg Luviskol VA64 | 1 mL EtOH | 7 mL 0.5 mg/mL NaOAc solution | Stable for 3 days at RT |
| 1.0 | 4 mg Luviskol VA64 | 1 mL EtOH | 7 mL 0.05 mg/mL NaOAc solution | Aggregated immediately |
| 1.0 | 4 mg Luviskol VA64 | 1 mL EtOH | 7 mL 0.5 mg/mL NaOAc solution | Aggregated within 1 day |
| 1.0 | 3 mg Luviskol VA64 | 1 mL EtOH | 0.0001M NaOH solution | Aggregated within 1 day |
| 1.0 | 3 mg Luviskol VA64 | 1 mL EtOH | 0.001M NaOH solution | Stable for 3 days at RT |
| 1.0 | 3 mg Luviskol VA64 | 1 mL EtOH | 0.01M NaOH solution | Stable for 3 days at RT |
| 1.0 | 3 mg Luviskol VA64 | 1 mL EtOH | 0.1M NaOH solution | Stable for 3 days at RT |

0.5 mg/ml solution of sodium dodecyl sulfate (SDS), dicotyl sodium sulfosuccinate (DSS) and sodium acetate (NaOAc) increased the stability of the redispersed sample yielding colloid solutions. However only the use of Luviskol VA64 as stabilizer and sodium acetate or sodium hydroxide aqueous solutions as anti-solvents resulted in colloids that were stable for up to 3 days at room temperature.

Optimization of the concentration of the necessary amount of sodium acetate has been performed. 0.5 mg/ml sodium acetate solution was selected based on stability of the redispersed solids in colloid solution. 0.001-0.1M sodium hydroxide solutions were used instead of sodium acetate solution as anti-solvents which also resulted is redispersible solid formulae. Significant decomposition of the active ingredient could be observed in HPLC analysis when 0.1 M sodium hydroxide used as antisolvent (data not shown). When 0.01 and 0.001 M sodium hydroxide solutions were used, decomposition of the active could not be observed. For the further experiments 0.001 M sodium hydroxide solution was used.

Two compositions or formulations 1 and 2 were selected (italic) and were produced at higher quantities for analytics.

4. Formulations

Formula 1
Active Starting Solution (in Ethanol):
    4 mg/ml of compound A
    12 mg/ml Luviskol VA64
Anti-Solvent (in Distilled Water):
    0.001 M Sodium hydroxide Nanoparticles were prepared in a microfluidic based continuous flow reactor. As a starting solution, 40 mg of compound A and 120 mg Luviskol VA64 dissolved in 100 mL ethanol was used. The prepared solution was passed into the reactor unit with 1 ml/min flow rate using a feeding unit. Meanwhile, using a second feeding unit, 0.001M sodium hydroxide solution in distilled water was passed into a mixing unit with 8 ml/min flow rate, where it was mixed with the solution containing compound A coming from the first reactor unit.

The nanoparticles are continuously produced at atmospheric pressure due to the chemical precipitation by water passed into the mixing unit. The produced colloidal solution driven through the second reactor unit reach the dynamic light scattering unit (Nanotrac) integrated to the device, which can detect the particle size of the obtained nanoparticle continuously. The produced colloid was lyophilized.

Formula 2
Active Starting Solution (in Ethanol):
    4 mg/ml of compound A
    12 mg/ml Luviskol VA64
Anti-Solvent (in Distilled Water):
    0.5 mg/ml Sodium acetate in distilled water Nanoparticles were prepared in a microfluidic based continuous flow reactor. As a starting solution, 40 mg of compound A and 120 mg Luviskol VA64 dissolved in 100 ml ethanol was used. The prepared solution was passed into the reactor unit with 1 ml/min flow rate using a feeding unit. Meanwhile, using a second feeding unit, 0.05 mg/mL sodium acetate dissolved in distilled water was passed into a mixing unit with 7 ml/min flow rate, where it was mixed with the solution containing compound A coming from the first reactor unit.

The nanoparticles are continuously produced at atmospheric pressure due to the chemical precipitation by water passed into the mixing unit. The produced colloidal solution driven through the second reactor unit reach the dynamic light scattering unit (Nanotrac) integrated to the device, which can detect the particle size of the obtained nanoparticle continuously. The produced colloid was lyophilized.

5. Characterization of Formulae 1 and 2

Redispersibility

The solid formulae were off-white, fluffy powders.

Compound A reference was not wetted by water, while redispersed nanoformulae 1 and 2 formed a slightly opalescent colloid solution practically instantaneously following the addition of water at room temperature.

Stability of the Redispersed Compound a Colloids

The particle size of the redispersed compound A colloids were measured by diffraction laser scattering (Nanotrac NPA-250 DLS instrument) immediately after redispersion.

| | |
|---|---|
| Formula 1 $d_{mean}$ - after redispersion | 431 nm |
| Formula 1 $d_{mean}$ - after 3 days | 262 nm |

| | |
|---|---|
| Formula 2 $d_{mean}$ - after redispersion | 264 nm |
| Formula 2 $d_{mean}$ - after 3 days | 245 nm |

The redispersed colloid solution were stable for at least 3 days at room temperature; no sedimentation or formation of aggregates were visible to the naked eye. Stability test was carried on for 14 days and the two solid nanosized formulae 1 and 2 were stable after 14 days of storage since no aggregation or appearance of solid particles could be seen.

Chemical Stability

Chemical stability of nanosized compound A formulae were investigated by HPLC measurements. They were performed in an Agilent 1100 HPLC waters coupled with ZQ2000 MSD, C18, Phenomenex Gemini-NX 3 micron, 100×3 mm column.

Based on the chromatograms of formula 1 and formula 2, no chemical decomposition of the active compound could be observed. The spectra are shown in FIG. 1.

Active Content

Determination of the active ingredients in solution was performed by spectrophotometry. Known quantities of reference active were dissolved in methanol. The UV absorbance of these solutions was measured at a characteristic wavelength (262 nm) and concentration-absorbance relationship, the calibration was calculated.

The active loading calculated from the initial concentrations are less than the measured values. In formula 2 the sublimation of acetic acid during the freeze drying formed from sodium acetate could result in the increase of active loading.

| | |
|---|---|
| Nominal active loading for formula 1 | 25% |
| Measured active loading for formula 1 | 30 ± 2% |

| | |
|---|---|
| Nominal active loading for formula 2 | 17% |
| Measured active loading for formula 2 | 27 ± 2% |

Solubility Measurement

Solid nanosized compound A was dispersed in distilled water at 0.5 mg/ml. The obtained colloid solution was stirred by intensive magnetic stirring (e.g. 750/min) for 10 minutes. After stirring the colloid was filtered with a Millex Durapore PVDF 100 nm syringe filter. The active loading of the filtrate was then determined.

Solubility of nanosized compound A was determined by filtration and UV-Vis measurements. The filtrate was a clear, translucent liquid. Nanoformulated compound A formulae 1 and 2 showed significant increase compared to the reference active:

| Formula 1 solubility | 0.61 ± 0.03 mg/ml |
|---|---|
| Formula 2 solubility | 0.59 ± 0.05 mg/ml |
| Reference solubility compound A | N.D* |

*Not Detected

Structural Analysis by Raman Spectrometry

The structure of nanosized compound A was investigated by Raman spectroscopy using a Yobin-Yvon/Horiba micro-Raman Spectrometer (Model: Labram) connected to an optical microscope with a 5, 10, 50 and 100× objective lenses (Olympus MPlan).

The Nb-YAG laser of 532 nm had a power of 50 mW at the source. The collected Raman radiation was dispersed with a 1200 lines mm$^{-1}$ grating (focal length 250 mm) and focused on a Peltier-cooled charge-coupled device CDD detector allowing to obtain a spectral resolution of ca 1 cm$^{-1}$. All spectra were recorded in the spectral window of 200-3600 cm$^{-1}$. The analysis time and number of accumulations to obtain a well-resolved raman spectrum vary depending on the excipients and the active ingredients.

Spectra collection was performed at room temperature under the following condition: 50× microscope objective with a D 0.6 filter, accumulation time was 10 s and the scan number was about 4 (these parameters were depended on the sample). The spectrum recording preformed with a CCD detector.

Structural analysis of nanosized compound A samples were performed by Raman spectrometry. The spectra of reference, nanosized compound A samples and the stabilizers are represented in FIG. 2.

Raman analysis showed that characteristic bands of reference compound A can be found in both nanosized samples. Band shifting of peak at 1314 cm$^{-1}$ can be observed which may indicate the formation of amorphous structure or presence of molecular interactions.

The characteristic peaks of sodium acetate cannot be observed in the formula 2 sample, which proves the elimination of acetic acid during the lyophilization step.

Residual Solvent Analysis of Formulae 1 and 2

Approximately 3×10 mg solid samples were measured into sample holder vials, 0.5 ml Triacetin aliquots were then added and the vials were closed immediately. Head Space Gas Chromatography (HSGC) was used to measure the amount of solvent in the solid formulations. 24 mg of the sample was placed in a tight, pressure resistant vial and residual solvents were determined.

HSGC analysis showed that residual ethanol content of the nanoformulae was negligible. It is well below the value quoted in the FDA (Food Drug Administration) guideline for Class 3 solvents (5000 ppm).

Example 2: Gel Formulations

Several gel compositions were prepared using formula 1 of the invention.

Gel composition 1-1 (containing 0.01% of nanosized compound A)

| Ingredients | Amount (% w/w) |
|---|---|
| Formula 1 | 0.045 |
| sodium acrylamide/acryloyldimethyltaurate copolymer/isohexadecane/polysorbate 80 | 4.0 |
| Methyl parahydroxybenzoate | 0.15 |
| Propyl parahydroxybenzoate | 0.03 |
| Purified water | 95.775 |

Manufacturing Process:
Phase 1:
In a vessel, weigh preservatives have been added to a part of purified water then stirred until complete dissolution.
Phase 2:
In a second vessel, weigh compound A nanosuspension has been added to the remaining water. The water redispersibility of compound A nanosuspension is instantaneous.
Phase 3:
The solution obtained in phase 2 has been added in the one obtained in phase 3 and then the gelling agent has been added.

At the end of the preparation a Microscopic observation (Axio Zeiss Microscope; magnitude ×40) is carried on and no crystal of compound A are observed in the gel composition of example 1-1 contrary to the reference micronized compound A (FIG. 3).

Gel composition 1-2 (containing 0.05% of nanosized compound A)

| Ingredients | Amount (% w/w) |
|---|---|
| Formula 1 | 0.226 |
| sodium acrylamide/acryloyldimethyltaurate copolymer/isohexadecane/polysorbate 80 | 4.0 |
| Methyl parahydroxybenzoate | 0.15 |
| Propyl parahydroxybenzoate | 0.03 |
| Purified water | 95.594 |

Manufacturing Process:
The Gel composition 1-2 is obtained using the procedure as above defined for the gel composition 1-1.
Stability of Gel Composition 1-1
The gel compositions 1-1 was stored at 4° C., ambient temperature (15-25° C.) and 40° C. over six months.
The results are illustrated in table 4.

TABLE 4

| Testing | Initial time | 1-Month | 3-Month | 6-Month |
|---|---|---|---|---|
| Appearance | | | | |
| RT | White gel | White gel | White gel | White gel |
| 4° C. | | White gel | White gel | White gel |
| 40° C. | | White gel | White gel | White gel |
| Microscopic analysis | | | | |
| RT | Very scarce crystals | Very scarce crystals | Scarce crystals | Scarce crystals |
| 4° C. | | | Scarce crystals | Scarce crystals |
|  | | | Scarce crystals | Scarce crystals |

TABLE 4-continued

| Testing | Initial time | 1-Month | 3-Month | 6-Month |
|---|---|---|---|---|
| 40° C. | | Scarce crystals | Scarce crystals | Scarce crystals |
| Compound A Assay (% initial) | | | | |
| RT | 100 | 99.6 | 110.5 | 99.9 |
| 40° C. | | 98.8 | 100.2 | 103.0 |

The gel formulation of the invention is physically and chemically stable over time.

Example 3: In Vitro Skin Release Study

Study Design:

The skin penetration of compound A nanosuspensions in topical formulations were studied using ex vivo skin penetration model.

These studies characterize the formulations of the invention by determining in vitro penetration of the active ingredient from the class of retinoids in different compartments of the skin. They also establish a classification of formulations of the invention in which they can promote or limit the penetration of the active ingredient, or target a specific compartment of the skin. The ability of a formulation to enter is a key with respect to a compound for topical application to skin which is a major barrier characteristic.

The skin penetration studies conducted on the formulations of the invention containing an active principle from the class of retinoids were carried out in vitro on human skin of the abdominal full after excision, the skin is mounted on a Franz cell. After topical application of a given formulation to the surface of the skin amount, penetration of the active ingredient was measured 16 h after application. The amount of active ingredient from the class of retinoids is measured in different compartments of the skin: the stratum corneum, epidermis, dermis and also in the receiving liquid.

Method:

2 mg/cm$^2$ of preparation was applied on dermatomed skin (850-1220 μm), and left for 16 hours.

The skin was washed with PEG400/Ethanol (70/30; w/w) solution, and the receptor fluid was PBS buffer.
- Number of cell/formulation: 6
- Number of donor/formulation: 3
- The results are expressed in ng/cm$^2$:
- Non absorbed dose
- Stratum corneum
- Epidermis
- Dermis
- Total skin (SC+Epidermis+Dermis)
- Absorbed dose
- Total penetrated (total skin+absorbed dose)

The bioassay was performed by tandem mass spectrometry in positive electrospray ionization, and using a Xevo (Waters) apparatus.

Formulations Tested:
Three types of formulations were tested:
- Formulation with solubilized compound A: solubilized compound A gel 0.01% reference (Solubilized Ref)
- Formulation with micronized compound A: micronized compound A gel 0.01% reference (Micronized Ref)
- Formulations with compound A nanosuspensions:
  Nanosuspension compound A gel 0.01% (Gel composition 1-1)
  Nanosuspension compound A gel 0.05% (Gel composition 1-2)

The results are represented in table 5.

TABLE 5

| | Solubilized Ref. 0.01% | | Micronized Ref 0.01% | | Gel composition 1-1 0.01% | | Gel composition 1-2 0.05% | |
|---|---|---|---|---|---|---|---|---|
| | Mean | SD | Mean | SD | Mean | SD | Mean | SD |
| Stratum corneum | | | | | | | | |
| ng/cm$^2$ | 13.43 | 2.30 | 6.31 | 2.70 | 7.28 | 2.41 | 28.30 | 14.09 |
| % applied dose | 7.12 | 1.43 | 3.04 | 1.28 | 3.55 | 1.13 | 2.69 | 1.33 |
| Epidermis | | | | | | | | |
| ng/cm$^2$ | 1.46 | 0.57 | 1.44 | 0.47 | 1.36 | 0.96 | 5.60 | 5.98 |
| % applied dose | 0.77 | 0.28 | 0.69 | 0.21 | 0.65 | 0.40 | 0.52 | 0.54 |
| Dermis | | | | | | | | |
| ng/cm$^2$ | 0.12 | 0.07 | 0.14 | 0.09 | 0.08 | 0.04 | 0.29 | 0.25 |
| % applied dose | 0.06 | 0.04 | 0.07 | 0.04 | 0.04 | 0.01 | 0.03 | 0.02 |
| Total skin | | | | | | | | |
| ng/cm$^2$ | 15.01 | 1.98 | 7.89 | 2.87 | 8.71 | 3.03 | 34.19 | 16.65 |
| % applied dose | 7.95 | 1.31 | 3.80 | 1.35 | 4.23 | 1.33 | 3.24 | 1.80 |
| Absorbed dose | | | | | | | | |
| ng/cm$^2$ | ILQ | ILQ | ILQ | ILQ | ILQ | ILQ | ILQ | ILQ* |
| % applied dose | ILQ | ILQ | ILQ | ILQ | ILQ | ILQ | ILQ | ILQ |
| Total penetrated | | | | | | | | |
| ng/cm$^2$ | 15.01 | 1.98 | 7.89 | 2.87 | 8.71 | 3.03 | 34.19 | 16.65 |
| % applied dose | 7.95 | 1.31 | 3.80 | 1.35 | 4.23 | 1.33 | 3.24 | 1.80 |

*Inferior Limit Quantification

The results shown that:
- the total penetration of compound A nanosuspensions formulated in gel compositions of the invention is lower when compared to solubilized compound A gel reference.
- the skin distribution of compound A nanosuspensions formulated in gel compositions of the invention in epidermis and dermis are quite similar to the ones obtained with solubilized compound A gel reference.
- the total penetrated amount and the compartmental analysis of compound A nanosuspensions formulated in gel compositions of the invention are similar to the ones obtained with micronized compound A gel reference.
- the compartmental distribution in epidermis and dermis of compound A nanosuspensions formulated in gel compositions of the invention is similar to the ones obtained with both solubilized and micronized compound A gel references.
- there is a dose proportionality between compound A nanosuspensions formulated in a gel 0.01% and a gel 0.05% in all the skin compartments.

The invention claimed is:
1. A nanosuspension, comprising:
(a) 25% to 35%, by weight, of water dispersible nanoparticles comprising only retinoid compound and having an average particle size of less than about 500 nm;

(b) 55% to 65%, by weight, of copolymers of vinyl pyrrolidone and vinyl acetate;

(c) a solvent comprising ethanol; and (d) an anti-solvent comprising an aqueous solution of 0.001-0.1 M sodium hydroxide, an aqueous solution of 0.001-0.1 M sodium acetate, or an aqueous solution comprising a mixture of sodium hydroxide and sodium acetate, which together have a concentration of 0.001-0.1 M, wherein the solvent and anti-solvent are miscible and the nanosuspension comprises no surfactant.

2. The nanosuspension according to claim 1, wherein the average particle size of the water dispersible nanoparticles is from about 50 nm to about 500 nm.

3. The nanosuspension according to claim 2, wherein the average particle size of the water dispersible nanoparticles is from about 200 nm to about 500 nm.

4. The nanosuspension according to claim 2, wherein the average particle size of the water dispersible nanoparticles is from about 250 nm to about 450 nm.

5. The nanosuspension according to claim 1, wherein the retinoid compound is selected from the group consisting of tretinoin, isotretinoin, adapalene, tazarotene, retinol, retinaldehyde, and a compound of formula (I):

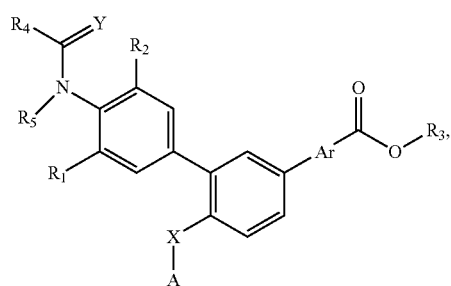

in which:

R1 represents a hydrogen atom, a C1-C4 alkyl group, or a —CF3 group;

R2 represents a hydrogen atom, a C1-C4 alkyl group, a C1-C4 alkoxy group, or a chorine atom;

R3 represents a hydrogen atom, a C1-C10 alkyl group or a C1-C10 alkoxy group optionally substituted with a methoxy group;

R4 and R5 represent, independently of each other, a hydrogen atom or a C1-C3 alkyl group, or alternatively, R4 and R5 form, together with the bond —N—C(=Y)—, a ring selected from the group consisting of pyrrolidine, pyrrolidone, piperidine, and piperidone;

Y represents two hydrogen atoms or a heteroatom,

Ar represents a 1,4-phenyl, 2,5-pyridyl, 5,2-pyridyl or 2,5-thiophenyl ring;

X represents an oxygen atom optionally substituted with a C1-C4 alkyl group or a C1-C4 alkylamino group, or a C—C single bond;

A represents a hydrogen atom or the following formula (IA):

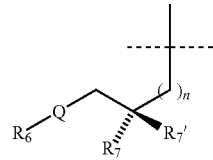

in which:

Q is an oxygen atom or an —NH— bond;

R6 represents a hydrogen atom, a C1-C6 alkyl group, a C3-C6 cycloalkyl group, a —C(O)CH3 group or a —C(O)CH2CH3 group;

R7 and R7' represent, independently of each other, a hydrogen atom, or a hydroxyl group, with the proviso that R7 and R7' are not simultaneously a hydroxyl group; and n=0, 1, 2, 3, 4 or 5;

and the optical and geometrical isomers thereof, and the pharmaceutically acceptable salts thereof.

6. The nanosuspension according to claim 5, wherein when Y is a heteroatom, the heteroatom is an oxygen or a sulfur.

7. The nanosuspension according to claim 1, wherein the retinoid compound is 3"-tert-butyl-4'-(2-hydroxyethoxy)-4"-pyrrolidin-1-yl[1,1';3',1"]-terphenyl-4-carboxylic acid.

8. The nanosuspension according to claim 7, comprising 0.001% to 10% by weight of the anti-solvent.

9. A pharmaceutical composition comprising a nanosuspension according to claim 1 in a pharmaceutically acceptable medium formulated for topical administration.

10. The pharmaceutical composition according to claim 9, wherein the composition is formulated in the form of a gel, an emulsion, a solution, a foam or a lotion.

11. The nanosuspension according to claim 10, wherein the composition is formulated in the form of a gel.

12. The pharmaceutical composition according to claim 9, wherein the composition further comprises at least one preservative.

13. The pharmaceutical composition according to claim 12, wherein the composition comprises, relative to the total weight of the pharmaceutical composition:

(a) 0.001% to 1% by weight of the nanosuspension; and (b) 0.001% to 1% by weight of the preservatives.

14. The nanosuspension according to claim 1, wherein the anti-solvent comprises the 0.001-0.1 M sodium hydroxide aqueous solution.

15. The nanosuspension according to claim 1, wherein the anti-solvent comprises the 0.001-0.1 M sodium acetate aqueous solution.

16. A process of preparing a nanosuspension according to claim 1, the process comprising:

(a) dissolving the retinoid compound and copolymers of vinyl pyrrolidone and vinyl acetate in the solvent to obtain a mixture;

(b) adding the mixture of (a) to a solution comprising the antisolvent to obtain a formulation; and (c) precipitating the formulation of (b) into a solid, thereby forming the nanosuspension.

17. The process according to claim 16, wherein the nanosuspension is prepared in a microfluidic based continuous flow reactor.

18. A method of treating a skin disease, the method comprising administering a pharmaceutical composition according to claim 9 to an individual subject having a skin disease.

19. The method according to claim 18, wherein the skin disease is selected from the group consisting of acne, ichthyosis and psoriasis.

\* \* \* \* \*